United States Patent [19]

Kummer et al.

[11] 3,941,848

[45] Mar. 2, 1976

[54] MANUFACTURE OF PREDOMINANTLY STRAIGHT-CHAIN ALDEHYDES

[75] Inventors: Rudolf Kummer, Frankenthal; Hans-Juergen Nienburg, Ludwigshafen; Heinz Hohenschutz, Mannheim; Max Strohmeyer; Theo Teutsch, both of Limburgerhof, all of Germany

[73] Assignee: Badische Anilin- & Soda-Fabrik Aktiengesellschaft, Ludwigshafen (Rhine), Germany

[22] Filed: July 24, 1973

[21] Appl. No.: 382,277

[30] Foreign Application Priority Data
July 29, 1972 Germany............................ 2237373

[52] U.S. Cl. .................... 260/604 HF; 260/617 HF
[51] Int. Cl.$^2$.......................................... C07C 45/08
[58] Field of Search .............................. 260/604 HF

[56] References Cited
UNITED STATES PATENTS

| | | | |
|---|---|---|---|
| 2,587,858 | 3/1952 | Keulemans .................. | 260/604 HF |
| 2,725,401 | 11/1955 | Mertzweiller et al......... | 260/604 HF |

FOREIGN PATENTS OR APPLICATIONS

| | | | |
|---|---|---|---|
| 36,106 | 3/1965 | Germany .................... | 260/601 |
| 702,241 | 1/1954 | United Kingdom .......... | 260/604 HF |
| 949,737 | 9/1956 | Germany .................... | 260/604 HF |

OTHER PUBLICATIONS

Treybal, Liquid Extraction; 2nd Edit., pp. 343–344, 1963.

Lemke, H., Chemical Abstracts, Vol. 62, col. 16040, 1965.

*Primary Examiner*—James O. Thomas, Jr.
*Assistant Examiner*—R. H. Liles
*Attorney, Agent, or Firm*—Johnston, Keil, Thompson & Shurtleff

[57] ABSTRACT

An improvement in the process for the manufacture of predominantly straight-chain aldehydes by hydroformylation of olefinically unsaturated compounds of 2 to 20 carbon atoms with carbon monoxide and hydrogen in which, in a first stage, aqueous cobalt solutions are treated with carbon monoxide and hydrogen at temperatures of 50° to 200°C and pressures of 100 to 400 atmospheres in the presence of active charcoal, zeolites or basic ion exchangers which are charged with cobalt carbonyl, in a second stage cobalt carbonyl-hydride is extracted from the reaction mixtures thus obtained, at temperatures of 20° to 180°C and pressures of 1 to 400 atmospheres, by means of olefinically unsaturated compounds which must be water-insoluble and liquid under the conditions used, the aqueous phase is separated off and the organic phase is transferred to a third stage and in this stage, after introducing olefinically unsaturated compounds if the latter have only been used partially for the extraction, the hydroformylation is carried out at temperatures of 70° to 170°C and pressures of 100 to 400 atmospheres, the improvement being that the extraction in the second stage is carried out as a co-current extraction whilst maintaining turbulent flow.

10 Claims, No Drawings

MANUFACTURE OF PREDOMINANTLY STRAIGHT-CHAIN ALDEHYDES

The invention relates to a process for the manufacture of predominantly straight-chain aldehydes by hydroformylation of olefins.

A process widely used in industry for the manufacture of aldehydes is the hydroformylation of olefins with carbon monoxide and hydrogen in the presence of cobalt carbonyl complexes. In the oxo synthesis, the catalytically active metal is usually added in the form of its salts, for example as an aqueous cobalt acetate solution. The catalytically active cobalt carbonyl complex then forms under the reaction conditions during the oxo synthesis. However, during the hydroformylation, significant amounts of undesired branched aldehydes are formed. Attempts have therefore already been made to control the hydroformylation of olefins, using cobalt carbonyl complexes modified with tertiary organic phosphines (compare DAS 1,186,455) in such a way that predominantly straight-chain oxo reaction products are formed. However, this process suffers from the disadvantage that the phosphines used are rapidly inactivated by slight traces of oxygen, which are difficult to exclude. Furthermore, the process referred to suffers from the disadvantage that the phosphine-modified catalysts can only be recovered at great expense and with some losses. For these reasons the process referred to has not found general acceptance in industry, even though it has been known for a considerable time.

A further problem which arises in using aqueous cobalt salt solutions is that a two-phase system is present during the hydroformylation and as a result the cobalt carbonyl-hydride, which is the actual active component, is not formed sufficiently rapidly and therefore an inhibition effect has to be overcome. It is known (compare German Patent Specification 946,621) that the difficulties in the hydroformylation of olefins with aqueous cobalt salt solutions which are attributable to two phase being present can be circumvented by carrying out the process in a high pressure tube filled with packings into which the aqueous cobalt salt solution is introduced from the top and the synthesis gas and the liquid olefin from the bottom, whilst aqueous catalyst solution is withdrawn at the bottom of the reactor to ensure that the aqueous phase does not accumulate at the lower end of the reactor. This process suffers from the disadvantage that it requires relatively high temperatures if adequate amounts of cobalt carbonyl-hydride are to be produced. A further known process (compare German patent specification No. 948,150) which uses aqueous cobalt salt solutions is to pre-carbonylate aqueous cobalt salt solutions at a higher temperature in the presence of an olefin and, after removing the aqueous solution, to hydroformylate at 180°C the olefin, containing cobalt carbonyl. Apart from the fact that the difficulties in the first stage mentioned above are not eliminated, the process also suffers from the disadvantage that insufficient cobalt carbonyl accumulates in the olefin. As a consequence, the hydroformylation must be carried out at high temperatures.

It is an object of the invention to provide a process which yields predominantly straight-chain aldehydes. It is another object of the invention to provide a process in which cobalt carbonyl-hydride is brought to the most active state for the hydroformylation in a simpler and less time-consuming manner.

In accordance with the present invention, these and other objects and advantages are achieved in an improved process for the manufacture of predominantly straight-chain aldehydes by hydroformylation of olefinically unsaturated compounds of 2 to 20 carbon atoms with carbon monoxide and hydrogen in which, in a first step, aqueous cobalt salt solutions are treated with carbon monoxide and hydrogen at temperatures of 50° to 200°C and pressures of 100 to 400 atmospheres in the presence of active charcoal, zeolites or basic ion exchangers which are charged with cobalt carbonyl, in a second stage cobalt carbonyl-hydride is extracted from the reaction mixture thus obtained, at temperatures of 20° to 180° and pressures of 1 to 400 atmospheres, by means of olefinically unsaturated compounds which must be water-insoluble and liquid under the conditions used, the aqueous phase is separated off and the organic phase transferred to a third stage and in this stage, after introducing olefinically unsaturated compounds, if the latter have only been used partially for the extraction, the hydroformylation is carried out at temperatures of 70° to 170°C and pressures of 100 to 400 atmospheres, the improvement being that the extraction in the second stage is carried out as a co-current extraction whilst maintaining turbulent flow.

The new process has the advantage that predominantly straight-chain aldehydes can be produced without using oxidizable phosphine complexes which are difficult to regenerate, and that a high olefin conversion is achieved. Furthermore, the new process has the advantage that the formation of alcohols is repressed and aldehydes are obtained almost exclusively. Moreover, the process has the advantage that the aqueous cobalt salt solution which is obtained when recovering the cobalt can be reused directly, without pretreatment, for example without concentrating it, as a cobalt salt solution for the manufacture of the catalyst. Finally, the new process has the advantage that the amount of cobalt carbonyl-hydride introduced into the oxo reaction can be controlled simply through the amount of aqueous cobalt salt solution introduced, without the need to introduce increased amounts of solvent, such as water, into the oxo reaction. A particular advantage of the new process is that the extraction of cobalt carbonyl-hydride is technically simpler and in particular requires very little time, so that considerably smaller equipment can be used. In addition, the extraction process is capable of giving better results.

In a first stage, aqueous cobalt salt solutions are treated with carbon monoxide and hydrogen at temperatures of 50° to 200°C and pressures of 100 to 400 atmospheres in the presence of active charcoal, zeolites or basic ion exchangers. Preferably, water-soluble cobalt salts of fatty acids, especially formates, acetates, propionates or butyrates, are used. Cobalt formate and cobalt acetate have proved particularly suitable. Suitable starting solutions contain 0.5 to 3 per cent by weight of cobalt, calculated as metal, especially 1 to 2 per cent by weight of cobalt, in the form of the salts mentioned. In general, the gas mixture referred to contains carbon monoxide and hydrogen in a volume ratio between 4 : 1 and 1 : 4, especially in a volume ratio between 2 : 1 and 1 : 2. The mixture of carbon monoxide and hydrogen is advantageously used in excess, for example in up to five times the stoichiometric amount. In the first step, either the entire amount of carbon monoxide and hydrogen required for the hydroformylation can be employed, or only a part thereof, for example 50 to 80% of the amount required for the hydroformylation.

The treatment in the first stage is carried out in the presence of active charcoal, zeolites or basic ion exchangers. Suitable types of active charcoal are, for example, peat charcoal, animal charcoal and sugar charcoal. Peat charcoal has proved particularly suitable. Preferred basic ion exchange resins contain primary, secondary or tertiary amino groups, and ion exchange resins which have become particularly important are those based on polystyrene and containing tertiary amino groups or quaternary amino groups in the base form. Particularly suitable ion exchangers are those which are weakly to strongly basic, examples being (R)Amberlite IR 45 and (R)Dowex 4. Macro-reticular types, such as (R)Amberlyst A 21, (R)Lewatit MP 62, (R)Lewatit MP 64, (R)Imac A 20, (R)Cerolite G, (R)Amberlite IRA 93 and (R)Amberlyst A 26 have attained particular importance in industry. It is desirable to charge the active charcoal, zeolites or basic ion exchangers with cobalt carbonyl until they are saturated. This is generally achieved by passing aqueous solutions of cobalt salts, together with the abovementioned gas mixture of carbon monoxide and hydrogen, over the active charcoal, zeolites or basic ion exchangers under the specified reaction conditions until they are saturated, that is to say until cobalt carbonyl or cobalt carbonyl-hydride is analytically detectable in the material which issues.

If active charcoal or zeolites are used, temperatures of 100° to 160°C have proved particularly favorable. On the other hand, if basic ion exchangers are also used, it is advisable to observe temperatures of 100° to 120°C. Pressures of 200 to 300 atmospheres have proved particularly advantageous.

In general, the treatment is carried out in a so-called treatment zone, the length to diameter ratio of which is appropriately between 5 and 50 : 1. A preferred throughput of metal is 1.5 to 50 g in the form of the abovementioned salts per hour and per kg of active charcoal, zeolites or basic ion exchangers.

In a second stage, cobalt carbonyl-hydride is extracted from the reaction mixture thus obtained, which contains cobalt salts and cobalt carbonyl-hydride, by means of olefinically unsaturated compounds which are liquid under the reaction conditions and are water-insoluble.

The essential characteristic of the invention is that the extraction is carried out as a co-current extraction whilst maintaining turbulent flow. The extraction is advantageously carried out in a so-called turbulence tube, that is to say in a zone having an L : D ratio of 100 to 10,000 : 1, which contains devices for maintaining a turbulent flow, such as packings, diaphragms or nozzles. An advantageous residence time in this zone is 5 to 60 seconds.

As a rule, the temperatures used are 20° to 180°C, especially 40° to 70°C, and the pressures used are 1 to 400 atmospheres, especially 250 to 300 atmospheres.

In an advantageous procedure, the aqueous solution containing cobalt salt and cobalt carbonyl-hydride and obtained in the first stage is introduced under the same pressure as into the second stage, without removing the gas mixture of carbon monoxide and hydrogen; in the second stage, the abovementioned mixture is extracted with olefinically unsaturated compounds which are liquid and water-insoluble under the reaction conditions, in co-current, at temperatures of 30° to 180°C, whilst observing the residence times mentioned.

In a further preferred procedure, the extraction in the extraction zone mentioned is carried out at the same pressure as is used in stage 1, but before the extraction the mixture of carbon monoxide and hydrogen is removed.

Another procedure which is to be recommended is to separate the aqueous solution containing cobalt salts and cobalt carbonyl-hydride and obtained in the first stage from the mixture of carbon monoxide and hydrogen, then to lower the pressure acting on the solution to normal pressure, and to carry out the extraction with olefinically unsaturated compounds which are liquid and water-insoluble under the reaction conditions, in co-current under normal pressure and at temperatures of 20° to 90°C. The extraction is best carried out in the presence of carbon monoxide or of a gas which is rich in carbon monoxide and which advantageously contains at least 70 per cent by volume of carbon monoxide in addition to inert substances such as hydrogen, nitrogen or argon. Advantageously, 2 to 20 liters of carbon monoxide or of the gas mixture mentioned are employed per liter of aqueous solution containing cobalt salts and cobalt carbonyl-hydride which are to be extracted.

Examples of suitable olefinically unsaturated compounds are olefins with 3 to 20 carbon atoms, $C_1$- to $C_4$-alkyl esters of unsaturated fatty acids with 3 to 18 carbon atoms, and unsaturated fatty acids and nitriles or vinyl esters and allyl esters of fatty acids with 2 to 8 carbon atoms. Examples of suitable extractants are pentene, hexene, octene, $C_8$- to $C_{10}$-olefin cuts or $C_{11}$- to $C_{14}$-olefin cuts, ethyl acrylate, butyl acrylate, ethyl crotonate, vinyl propionate, allyl acetate, acrylic acid and acrylonitrile. It is particularly preferred to use olefins which are used as starting substances in the subsequent oxo reaction.

It is also possible to mix the olefinically unsaturated compounds with up to 90% of hydrocarbons, such as paraffins, cycloparaffins or aromatic hydrocarbons which are liquid under the extraction conditions, such as benzene, toluene, xylene, cyclohexane or octane. This procedure is advisable if the olefinically unsaturated compounds used are water-soluble, as they are thereby converted into a water-insoluble form.

It is advantageous to use between 0.5 and 5 liters of olefinically unsaturated compounds as the extractant per liter of aqueous solution containing cobalt salts and cobalt carbonyl-hydride. The cobalt content of the organic phase leaving the second stage is generally between 0.05 and 2 per cent by weight. It goes without saying that a separation into an organic phase and an aqueous phase is carried out during the extraction. It is desirable at the same time also to separate off the carbon monoxide or the gas rich in carbon monoxide.

The resultant organic phase containing cobalt carbonyl-hydride, and the mixture of carbon monoxide and hydrogen, or the organic phase alone, are transferred to a third stage and are there hydroformylated at temperatures of 70° to 170°C and pressures of 100 to 400 atmospheres, if necessary after introducing the requisite amount of olefinically unsaturated compounds, if only a part of these has been used for the extraction in the abovementioned stage. Temperatures of 80° to 130°C and pressures of 200 to 300 atmospheres have proved particularly suitable. If the entire amount of carbon monoxide and hydrogen required for the hydroformylation has not already been introduced in the first stage, the amounts still required are introduced in the third stage so that at least the stoichiometric amount of carbon monoxide and hydrogen, but preferably an excess of up to 100 mole per cent, is available per mole of olefin.

It is advantageous to flash the hydroformylation mixture leaving the third stage to between 1 and 10 atmospheres and to treat the mixture, for example at temperatures of 80° to 160°C and preferably 105° to 150°C, with gases containing molecular oxygen, especially air, in at least the stoichiometric amount relative to cobalt, and with an aqueous weakly acid cobalt salt solution of 0.5 to 3 per cent strength by weight. It is preferred to use the aqueous phase obtained in the second stage, which still contains 0.1 to 0.8 per cent by weight of cobalt in the form of the salts mentioned in connection with the second stage, and to mix this phase with cobalt salt solution from the cobalt removal stage; this gives an aqueous phase containing 1 to 3 per cent by weight of cobalt. The acids contained in the hydroformylation mixture automatically give a pH value of, preferably, 3.5 to 4.5. It is advantageous to use 3 to 30 liters (S.T.P.) of air and 0.5 to 2 liters of the aqueous cobalt salt solution mentioned per kg of hydroformylation mixture. It is advantageous to recycle the cobalt salt solution so that the cobalt content increases to between 1 and 3 per cent by weight; the cobalt acetate solution which has been enriched in this way is then withdrawn continuously and replaced at the same rate by the aqueous phase from the second stage. The aqueous cobalt salt solution, now enriched in cobalt salts, which has been withdrawn, is preferably returned to the first stage and used as the starting solution therein. The duration of the treatment is advantageously 0.5 to 5 minutes. After removing the gas phase, the organic phase is worked up according to known methods, for example by distillation, or is directly transferred to the hydrogenation step so as to produce the corresponding alcohols.

Aldehydes which are manufactured by the process of the invention are suitable for the manufacture of alcohols, especially alcohols for detergent purposes and for plasticizers, and also for the manufacture of carboxylic acids and of amines.

The examples which follow are intended to illustrate the process.

EXAMPLE 1

20 ml of an aqueous cobalt formate solution containing 1.8 per cent by weight of cobalt are introduced hourly, from below, into a high pressure tube of 0.5 l capacity, and 30 mm diameter which is filled with 180 g of peat charcoal grade AKT IV, of particle size 3.4 to 4.5 mm. Additionally, 120 l of an equimolecular mixture of carbon monoxide and hydrogen are introduced. The temperature is maintained at 140°C and the pressure at 280 atmospheres gauge. The solution issuing at the top contains 0.4 per cent by weight of divalent cobalt and 1.6 per cent by weight of cobalt as cobalt carbonyl-hydride. This solution, together with the mixture of carbon monoxide and hydrogen which issues, is passed to the extraction stage.

A pressure turbulence tube of stainless steel, 110 cm in length and 4 mm in internal diameter, provided with a steam heating jacket, is filled with glass beads (diameter about 3 to 4 mm). The free space in the tube is 5 cm³. The temperature in the steam heating jacket is 117°C. The tube is fed at one end with the following quantities per hour: 800 ml of a $C_8$–$C_{10}$-α-olefin mixture, 300 ml of a pre-carbonylated aqueous cobalt formate solution (0.32% of $Co^{2+}$, 0.68% of Co as HCo(CO)$_4$) and 270 liters (S.T.P.) of oxo gas. The pressure in the tube is 280 atmospheres. The average residence time in the tube is calculated to be about 9 seconds. The temperature of the mixture at the end of the tube is 66°C. The mixture leaving the turbulence tube separates into three phases in a calming vessel. The gas phase and the olefinic phase containing cobalt carbonyls (0.32 % Co), are fed to the oxo reactor under the same pressure, whilst the aqueous phase (0.31% of $Co^{2+}$ and 0.05% of Co as HCo(CO)$_4$) is flashed to atmospheric pressure. 94% of the extractable cobalt are extracted.

The α-olefin misture containing cobalt carbonylhydride is made up with the necessary amount of carbon monoxide and hydrogen and then hydroformylated at a temperature of 120°C and a pressure of 280 atmospheres. The reaction product obtained is treated with 1 l of air and 120 ml of aqueous cobalt acetate solution containing acetic acid and about 1.8% by weight of cobalt, at 200°C. Analysis by gas chromatography of the cobalt-free organic material which issues shows 72.2% of n-butyraldehyde, 18.0% of i-butyraldehyde, 1.2% of butanols, 5.0% of butyl formates and 4% of high-boiling constituents.

EXAMPLE 2

The procedure described in Example 1 is adopted but the extraction is carried out as follows:

A turbulence tube made of glass, 110 cm in length and 4 mm in internal diameter, is provided with a heating jacket and filled with glass beads (3 to 4 mm diameter). The free space in the tube is 4.5 cm³. The heating jacket is kept at a temperature of 60°C by means of warm water. The tube is charged with the following quantities hourly: 1,000 ml of octene-1 and 320 ml of a pre-carbonylated aqueous cobalt formate solution containing 0.24% of $Co^{2+}$ and 0.54% of Co as HCo(CO)$_4$. Apart from the small amounts of dissolved carbon monoxide and hydrogen present in the pre-carbonylated solution, no further gas is introduced. The mean residence time in the tube is calculated to be 12 seconds. The mixture leaving the turbulence tube separates into two phases in a calming vessel. The olefinic phase contains 0.22% of Co as cobalt carbonyls. It is compressed to 280 atmospheres and passed to the oxo reactor. The aqueous phase contains 0.26% of $Co^{2+}$ and 0.04% of Co as HCo(CO)$_4$. Hence, 89% of the extractable cobalt have actually been extracted. In the subsequent hydroformylation, good results similar to those in Example 1 are obtained.

EXAMPLE 3

The procedure described in Example 1 is adopted, but the extraction is carried out as follows:

The turbulence tube described in Example 2 is fed with 400 ml of a $C_{11}$–$C_{14}$-α-olefin mixture and 200 ml of a pre-carbonylated cobalt formate solution (0.28% of $Co^{2+}$ and 0.47% of Co as HCo(CO)$_4$) under the same conditions as in Example 2. After separation in the calming vessel the olefinic phase contains 0.26% of Co as HCo(CO)$_4$ and the aqueous phase contains 0.32% of $Co^{2+}$ and 0.03% of Co as HCo(CO)$_4$. Hence, 85% of the extractable cobalt have been extracted. The hydroformylation gives good results similar to those in

We claim:

1. In an improved process for the manufacture of predominantly straight-chain aldehydes by hydroformylation of olefinically unsaturated compounds of 2 to 20 carbon atoms with carbon monoxide and hydrogen in which, in a first stage; aqueous cobalt salt solutions are treated with carbon monoxide and hydrogen at a temperature of 50° to 200°C and a pressure of 100 to 400 atmospheres in the presence of active charcoal, zeolites or basic ion exchangers which are charged with cobalt carbonyl, in a second stage cobalt carbonylhydride is extracted from the resultant reaction mixture at a temperature of 20° to 180°C and a pressure of 1 to 400 atmospheres by means of olefinically unsaturated compounds which are water-insoluble and liquid under the conditions used, the aqueous phase is separated from said liquid olefinically unsaturated compounds containing extracted cobalt carbonyl-hydride, and latter liquid is transferred to a third stage and in this stage, after introducing olefinically unsaturated compounds if the latter have only been used partially for the extraction, the hydroformylation is carried out at a temperature of 70° to 170°C and under a pressure of 100 to 400 atmospheres, the improvement comprising carrying out the extraction in the second stage as a cocurrent extraction while maintaining turbulent flow of said aqueous phase and said liquid olefinically unsaturated compounds during said cocurrent extraction.

2. Process according to claim 1, wherein a residence time of 5 to 60 seconds is used in the extraction.

3. Process according to claim 1, wherein the length to diameter ratio of the extraction zone is between 100 and 10,000 : 1.

4. Process according to claim 1, wherein olefins with 3 to 20 carbon atoms, which are used for the hydroformylation, are employed as extractants.

5. A process as claimed in claim 1, wherein the extraction zone of the extraction in the second stage is tube means having a length to diameter ratio in the range of 100:1 to 10,000:1, and the turbulence in said zone being provided by packings, diaphragms or nozzles in said tube means.

6. In a process for the extraction of cobalt carbonylhydride from an aqueous solution at a temperature of 20° to 180°C and a pressure of 1 to 400 atmospheres with a liquid olefinically unsaturated compound which is water-soluble and liquid under the conditions used, the improvement comprising carrying out the extraction cocurrently while maintaining turbulent flow of said aqueous solution and said liquid olefinically unsaturated compounds in the extraction zone.

7. A process as claimed in claim 6 wherein the residence time for said extraction of the aqueous solution and olefinically unsaturated compound is in the range of 5 to 60 seconds.

8. A process as claimed in claim 7 wherein the extraction zone has a length to diameter ratio in the range of 100:1 to 10,000:1.

9. A process as claimed in claim 1 wherein said olefinically unsaturated compound is an olefin with 3 to 20 carbon atoms.

10. A process as claimed in claim 7, wherein the extraction zone of the extraction in the second stage is tube means having a length to diameter ratio in the range of 100:1 to 10,000:1, and the turbulence in said zone being provided by packings, diaphragms or nozzles in said tube means.

* * * * *